US011805620B2

(12) United States Patent
Konkle et al.

(10) Patent No.: US 11,805,620 B2
(45) Date of Patent: Oct. 31, 2023

(54) COMPUTED TOMOGRAPHY THERMAL MANAGEMENT SYSTEM AND METHOD FOR OPERATION OF SAID SYSTEM

(71) Applicants: GE Precision Healthcare LLC, Wauwatosa, WI (US); Prismatic Sensors AB, Stockholm (SE)

(72) Inventors: Nicholas Konkle, Sussex, WI (US); Eric Aasen, Pewaukee, WI (US); Scott Slavic, Wauwatosa, WI (US); Kyle Reiser, Waukesha, WI (US); Michael Boehm, Waukesha, WI (US); Mats Hedberg, Vendelso (SE)

(73) Assignees: GE Precision Healthcare LLC, Wauwatosa, WI (US); Prismatic Sensors AB, Stockholm (SE)

( * ) Notice: Subject to any disclaimer, the term of this patent is extended or adjusted under 35 U.S.C. 154(b) by 28 days.

(21) Appl. No.: 17/463,049

(22) Filed: Aug. 31, 2021

(65) Prior Publication Data
US 2022/0071057 A1    Mar. 3, 2022

Related U.S. Application Data

(60) Provisional application No. 63/072,622, filed on Aug. 31, 2020.

(51) Int. Cl.
*H05K 7/20* (2006.01)
*G01T 7/00* (2006.01)

(52) U.S. Cl.
CPC ........... *H05K 7/20263* (2013.01); *G01T 7/00* (2013.01); *H05K 7/20136* (2013.01); *H05K 7/20272* (2013.01)

(58) Field of Classification Search
CPC .......... H05K 7/20263; H05K 7/20136; H05K 7/20272; G01T 7/00
USPC ........................................................ 361/695
See application file for complete search history.

(56) References Cited

U.S. PATENT DOCUMENTS

| 5,285,347 | A | * | 2/1994 | Fox | G06F 1/20 257/714 |
| 5,473,508 | A | * | 12/1995 | Porter | H01L 23/467 257/713 |
| 6,775,137 | B2 | * | 8/2004 | Chu | H05K 7/20754 361/679.54 |
| 6,807,056 | B2 | * | 10/2004 | Kondo | H05K 7/20781 361/689 |

(Continued)

OTHER PUBLICATIONS

International Application No. PCT/US2021/048517 filed Aug. 31, 2021—International Search Report and Written Opinion dated Nov. 30, 2021; 13 pages.

*Primary Examiner* — Anatoly Vortman (57) ABSTRACT

A thermal management system and method for cooling a CT detector assembly of a CT imaging system. The thermal management system uses a combination of air cooling for the readout electronics of the CT detector assembly and liquid cooling for the X-ray sensors of the CT detector assembly. The hybrid air and liquid cooling systems and methods may be coupled together in the thermal management system and method to create a cooler temperature in the CT detector assembly. The CT detector assembly components may include CT detector modules, which may include X-ray sensors, readout electronics and other components.

9 Claims, 8 Drawing Sheets

(56) References Cited

U.S. PATENT DOCUMENTS

| | | | |
|---|---|---|---|
| 6,807,812 B2* | 10/2004 | Lehmann | G01R 33/3815 |
| | | | 165/185 |
| 6,819,563 B1* | 11/2004 | Chu | H05K 7/20736 |
| | | | 165/104.33 |
| 11,322,299 B2* | 5/2022 | Walser | A61B 5/6878 |
| 2004/0020218 A1* | 2/2004 | Alford | G01R 33/34 |
| | | | 165/185 |
| 2005/0117698 A1* | 6/2005 | Lacey | A61B 6/035 |
| | | | 378/19 |
| 2006/0109956 A1* | 5/2006 | Lacey | A61B 6/035 |
| | | | 378/199 |
| 2010/0188082 A1* | 7/2010 | Morich | G01R 33/481 |
| | | | 250/363.04 |
| 2012/0123237 A1* | 5/2012 | Canzolino | A61B 6/045 |
| | | | 600/407 |
| 2013/0037251 A1* | 2/2013 | Joshi | G05D 23/1919 |
| | | | 378/19 |
| 2013/0279648 A1 | 10/2013 | Joshi | |
| 2016/0174920 A1* | 6/2016 | Lacey | A61B 6/4488 |
| | | | 378/189 |
| 2018/0133518 A1 | 5/2018 | Harper | |
| 2018/0303437 A1 | 10/2018 | Fortuna | |
| 2022/0071057 A1* | 3/2022 | Konkle | H05K 7/20136 |

* cited by examiner

COMPUTED TOMOGRAPHY THERMAL MANAGEMENT SYSTEM AND METHOD FOR OPERATION OF SAID SYSTEM

CROSS-REFERENCE TO RELATED APPLICATIONS

This application claims the benefit of and priority to U.S. Provisional Application No. 63/072,622, filed on Aug. 31, 2020, the disclosure of which is incorporated herein by reference in its entirety.

BACKGROUND

Embodiments of the subject matter disclosed herein relate to computed tomography (CT) imaging systems with thermal management systems and methods for operation of said systems.

Computed tomography (CT) imaging systems are used to generate images of subjects (e.g., patients) or objects. For instance, some CT imaging systems include rotating gantries directing targeted X-ray beams toward the subject or object being scanned. However, CT imaging systems present various thermal management challenges. A CT imaging system typically includes a CT detector assembly within a rotating gantry. The CT detector assembly may be a high-power consuming component with limited cooling capacity in the rotating gantry. The CT detector assembly components, such as detector modules, which may include X-ray sensors, readout electronics and other components generate heat while the CT scanner operates. These components may have different cooling needs and previous CT imaging systems may not be able to meet the cooling requirements of CT detector assembly components. Therefore, there is a need for an improved thermal management system and method for operation of same in a CT imaging system, especially for cooling the CT detector assembly.

SUMMARY

This summary introduces aspects and features that are described in more detail in the detailed description. It should not be used to identify essential features of the claimed subject matter, nor to limit the scope of the claimed subject matter.

In one aspect, a thermal management system for a CT imaging system includes a liquid cooling assembly including a liquid coolant pumped through a closed loop conduit from a heat exchanger and a liquid coolant temperature controller through a CT detector assembly and back to the heat exchanger and liquid coolant temperature controller, the liquid coolant assembly including a first plurality of fans configured to pull inlet air from the outside to flow over the closed loop liquid conduit with temperature control to cool a liquid coolant and exhaust air to outside of the thermal management system; and an air cooling assembly coupled to the liquid coolant assembly, the air cooling assembly including a second plurality of fans configured to pull inlet air from outside the thermal management system to flow over a rail radiator, the closed loop conduit, the CT detector assembly and exhaust air to outside of the thermal management system.

In another aspect, a thermal management system for a CT imaging system includes a liquid cooling assembly including a coolant conduit routing liquid coolant from a heat exchanger to a rail and from the rail to a rail radiator and back to the heat exchanger; and a coolant pump coupled to the coolant conduit to pump the liquid coolant through the coolant conduit; a plurality of CT detector modules coupled to a first side of the rail; a plurality of detector hardware components coupled to a second side of the rail, positioned in an airflow duct, and in electronic communication with the plurality of CT detector modules; and an air cooling assembly including a plurality of fans positioned in a plurality of outlet openings in the airflow duct; and a rail radiator positioned in an inlet opening of the airflow duct.

In yet another aspect, a method for operating a thermal management system in a CT imaging system includes operating a coolant pump in a liquid cooling assembly to generate liquid coolant flow through a coolant conduit, wherein the coolant pumps liquid coolant through the coolant conduit from a heat exchanger to a rail and from the rail to a rail radiator, wherein the rail radiator is positioned in an airflow duct, and wherein a plurality of CT detector modules are coupled to a first side of the rail; and operating a plurality of fans in an air cooling assembly, the plurality of fans positioned in a plurality of outlet openings of the airflow duct to generate airflow through the airflow duct, and wherein a plurality of detector hardware components are positioned within the airflow duct.

The above advantages, aspects, and features of the present description will be readily apparent from the following detailed description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Embodiments of the present disclosure will now be described, by way of example, with reference to figures in the drawings. Thermal management systems in computed tomography (CT) imaging systems and methods for operation of the thermal management systems for achieving increased CT component cooling are described herein. The thermal management systems and methods also, in some exemplary embodiments, allow the thermal management or cooling system to achieve higher levels of component cooling in comparison to previous CT cooling systems.

The present disclosure describes and illustrates a thermal management system for cooling a CT detector assembly of a CT imaging system. The thermal management system may include a combination of air cooling and liquid cooling for cooling the CT detector assembly. The air and liquid cooling systems may be coupled together in the thermal management system to cool the components of the CT detector assembly. The CT detector assembly may include a plurality or array of detector modules, which may include X-ray sensors, readout electronics and other components.

Figure 1:
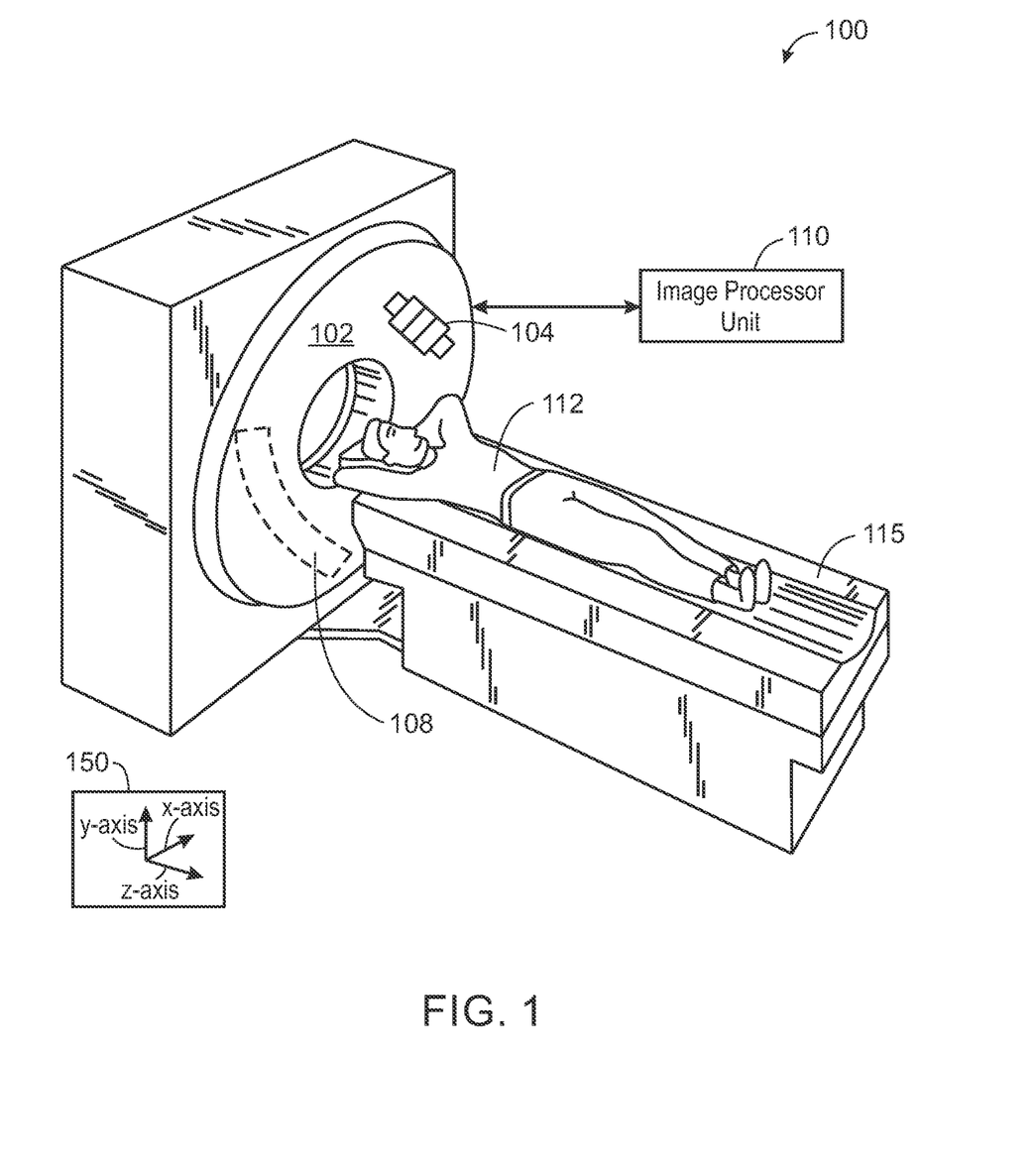
FIG. 1 is a perspective view of an exemplary CT imaging system.

FIG. 1 illustrates an exemplary CT imaging system 100. Particularly, the CT imaging system 100 is configured to image a subject 112 such as a patient, an inanimate object, one or more manufactured parts, and/or foreign objects, such as implants, and/or contrast agents present within a body. In one exemplary embodiment, the CT imaging system 100 includes a gantry 102, which in turn, may further include at least one X-ray source 104 configured to project a beam of X-ray radiation 106 (see FIG. 2) for use in imaging the subject 112 laying on a table 115. Specifically, the X-ray source 104 is configured to project an X-ray beam 106 towards an X-ray detector 108 positioned on the opposite side of the gantry 102 from the X-ray source 104. Although FIG. 1 depicts only a single X-ray source 104, in certain exemplary embodiments, multiple X-ray sources and detectors may be employed to project a plurality of X-ray beams for acquiring projection data at different energy levels corresponding to the patient.

In some exemplary embodiments, the X-ray source 104 may enable dual-energy gemstone spectral imaging (GSI) by rapid peak kilovoltage (kVp) switching. In some exemplary embodiments, the X-ray detector employed is a photon-counting detector which is capable of differentiating X-ray photons of different energies. In other exemplary embodiments, two sets of X-ray sources and detectors are used to generate dual energy projections, with one set at low kVp and the other at high kVp. However, numerous suitable X-ray detector configurations have been envisioned. It should thus be appreciated that the systems and methods described herein may be implemented with single energy acquisition techniques as well as dual energy acquisition techniques.

In certain exemplary embodiments, the CT imaging system 100 further includes an image processor unit 110 configured to process or reconstruct images of a region of interest or target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), or any other iterative image reconstruction technique to reconstruct images of a target volume of the subject 112.

In some CT imaging system configurations, an X-ray source projects a cone-shaped or fan-shaped X-ray beam which is collimated to lie within an x-y-z plane of a Cartesian coordinate system and generally referred to as an "imaging plane." The X-ray beam passes through a subject or object being imaged. The X-ray beam, after being attenuated by the subject or object, impinges upon an array of X-ray detector modules. The intensity of the attenuated X-ray beam received at the array of X-ray detector modules is dependent upon the attenuation of the X-ray beam by the subject or object. Each X-ray detector module of the X-ray detector array produces a separate electrical signal that is a measurement of the X-ray beam attenuation at the X-ray detector module location. The X-ray attenuation measurements from all of the X-ray detector modules are acquired separately to produce a transmission profile.

In some CT imaging systems, the X-ray source and the X-ray detector array are rotated within a gantry around the subject or object to be imaged such that an angle at which the X-ray beam intersects the object constantly changes. A group of X-ray attenuation measurements, e.g., projection data, from the X-ray detector array at one gantry angle is referred to as a "view." A "scan" of the subject or object includes a set of views made at different gantry angles, or view angles, during one revolution of the X-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, magnetic resonance (MR), positron emission tomography (PET), single-photon emission CT (SPECT), or X-ray acquisition, and/or any other imaging modality including modalities yet to be developed, as well as combinations thereof (e.g., multi-modality imaging systems, such as PET/CT, PET/MR or SPECT/CT imaging systems).

The projection data is processed to reconstruct an image that corresponds to a two-dimensional slice taken through the object or, in some examples where the projection data includes multiple views or scans, a three-dimensional rendering of the object.

An illustration of a Cartesian coordinate system 150 is provided in FIG. 1 as well as FIGS. 3-6, for reference. The Cartesian coordinate system showing the proper orientations of an x-axis, a y-axis, and a z-axis as they relate to the CT imaging system 100. The x-axis may be in a lateral direction, the y-axis may be in a vertical direction, and the z-axis may be in a longitudinal direction (e.g., rotational axis of the gantry). However, the axes may have other orientations, in other examples.

Figure 2:
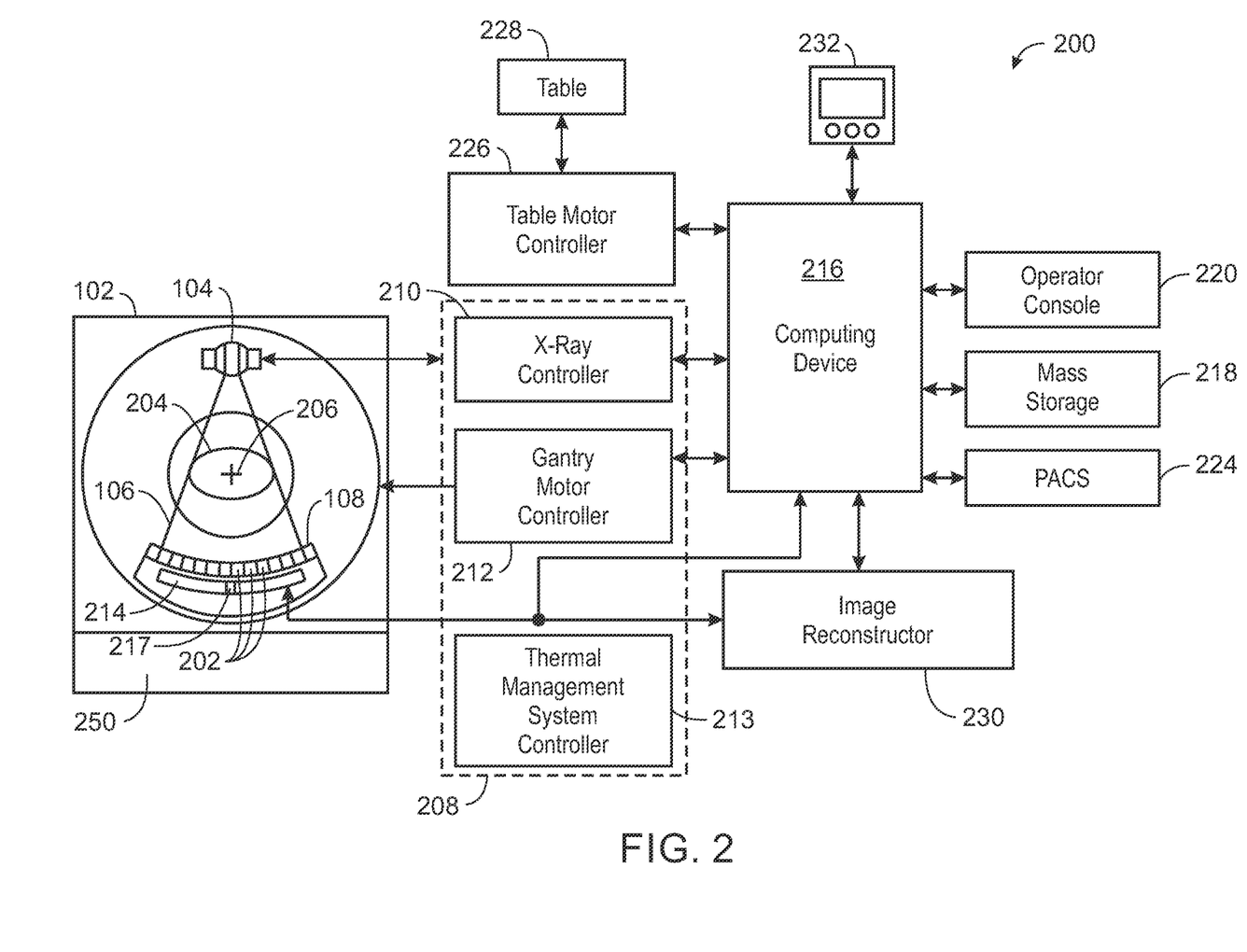
FIG. 2 is a schematic block diagram of an exemplary CT imaging system.

FIG. 2 illustrates a schematic block diagram of an exemplary CT imaging system 200, similar to the CT imaging system 100 of FIG. 1. In accordance with aspects of the present disclosure, the CT imaging system 200 is configured for imaging a subject 204 (e.g., the subject 112 of FIG. 1). In one exemplary embodiment, the CT imaging system 200 includes an X-ray detector array 108 (also known as a CT detector array or a CT detector assembly). The X-ray detector array 108 further includes a plurality of X-ray detector modules or CT detector modules 202 that together sense the X-ray beam 106 that passes through the subject 204 (such as a patient 112 in FIG. 1) to acquire corresponding projection data. Accordingly, in one exemplary embodiment, the CT detector array 108 is fabricated in a multi-slice configuration including a plurality of rows of CT detector modules 202. In such a configuration, one or more additional rows of CT detector modules 202 may be arranged in a parallel configuration for acquiring projection data.

In certain exemplary embodiments, the CT imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the X-ray source 104 and the X-ray detector array 108 rotate, the X-ray detector array 108 collects data of the attenuated X-ray beams. The data collected by the X-ray detector array 108 undergoes pre-processing and calibration to condition the data to represent the line integrals of the attenuation coefficients of the scanned subject 204. The processed data are commonly called projections.

In some examples, the individual CT detector modules 202 of the CT detector array 108 may include photon-counting detector modules which register the interactions of individual photons into one or more energy bins. It should be appreciated that the methods described herein may also be implemented with energy-integrating CT detector modules. In an exemplary embodiment, the CT detector modules 202 may be photon-counting detector modules or another type of detector module with a relatively high energy usage.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the region of interest or imaged target volume.

Once reconstructed, the basis material image produced by the CT imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular lesions, anatomies or organs, and other features that would be discernable in the image based upon the skill and knowledge of the individual practitioner.

In one exemplary embodiment, the CT imaging system 200 includes a control system 208 to control various components of the CT imaging system, such as operation of the X-ray source 104, rotation of the gantry 102 and operation of a thermal management system for the CT detector assembly 108. In certain exemplary embodiments, a control system 208 further includes an X-ray controller 210 configured to provide power and timing signals to the X-ray source 104, a gantry motor controller 212 configured to control the rotational speed and/or position of the gantry 102 based on imaging requirements, and a thermal management system controller 213 to provide cooling to the CT detector assembly 108.

In certain exemplary embodiments, the control system 208 further includes a data acquisition system (DAS) 214 configured to sample analog data received from the CT detector modules 202 and convert the analog data to digital signals for subsequent processing. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive. The DAS 214 may include detector electronics 217 (e.g., readout electronics and other components) configured for detector signal acquisition and processing. For example, the detector electronics 217 may include analog to digital converters, digital signal processors, amplifiers, etc., designed to process detector signals from the CT detector modules. The DAS 214 may further include one or more storage devices or mass storage elements to store image data within the DAS for data processing, long term storage, or temporary storage.

Additionally, the computing device 216 provides commands and parameters to one or more of the DAS 214, the X-ray controller 210, the gantry motor controller 212, and the thermal management system controller 213 for controlling system operations such as data acquisition and/or processing. In certain exemplary embodiments, the computing device 216 controls system operations based on operator input. The computing device 216 receives the operator input, for example, including commands and/or scanning parameters via a workstation or an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the CT imaging system 200, for example, for inputting or outputting system parameters, requesting examinations, graphing data, and/or viewing images. Further, in certain exemplary embodiments, the CT imaging system 200 may be coupled to multiple displays, printers, workstations, and/or similar devices located either locally or remotely, for example, within a facility or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the CT imaging system 200 either includes, or is coupled to, a picture archiving and communications system (PACS) 224. In an exemplary implementation, the PACS 224 is further coupled to a remote system such as a radiology information system (RIS), hospital information system (HIS), and/or to an internal or external network (not shown) to allow operators at different locations to supply commands and parameters and/or gain access to the image data.

The computing device 216 uses the operator supplied and/or system defined commands and parameters to operate a table motor controller 226, which in turn, may control a table 228 (e.g., the table 115 in FIG. 1) which may be a motorized table. Specifically, the table motor controller 226 may move the table 228 for appropriately positioning the subject 204 within an opening of the gantry 102 for acquiring projection data corresponding to the target volume of the subject 204.

As previously noted, the DAS 214 samples and digitizes the projection data acquired by the CT detector modules 202. Subsequently, an image reconstructor 230 uses the sampled and digitized X-ray data to perform high-speed reconstruction. Although FIG. 2 illustrates the image reconstructor 230 as a separate entity, in certain exemplary embodiments, the image reconstructor 230 may form part of the computing device 216. Alternatively, the image reconstructor 230 may be absent from the CT imaging system 200 and instead the computing device 216 may perform one or more functions of the image reconstructor 230. Moreover, the image reconstructor 230 may be located locally or remotely, and may be operatively connected to the CT imaging system 200 using a wired or wireless network. Particularly, one exemplary embodiment may use computing resources in a "cloud" network cluster for the image reconstructor 230.

In one exemplary embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain exemplary embodiments, the computing device 216 may transmit the reconstructed images and/or the patient information to a display or display device 232 communicatively coupled to the computing device 216 and/or the image reconstructor 230. In some exemplary embodiments, the reconstructed images may be transmitted from the computing device 216 or the image reconstructor 230 to the storage device 218 for short-term or long-term storage.

The CT imaging system 200 also include a thermal management system 250. The thermal management system 250 is designed to provide cooling to various components in the CT imaging system such as the CT detector assembly 108. Although, the thermal management system 250 and components therein along with other CT imaging system components are schematically depicted in FIG. 2, it will be understood that the thermal management system has greater structural complexity than is captured in FIG. 2. Structural as well as functional features of the thermal management system 250 are expanded upon in greater detail herein with regard to FIGS. 3-9.

The thermal management system 250 may be controlled via the thermal management system controller 213 in the control system 208, which may include one or more processor, memory, and/or other electronics or hardware for carrying out thermal management system control. The various methods and processes (such as the method described below with reference to FIGS. 7-9) described in more detail herein may be stored as executable instructions in non-transitory memory of the thermal management system controller 213 or other suitable computing device in CT imaging system 200, such as the computing device 216 (or other controller/processor) in the CT imaging system 200 to adaptively control thermal management of the CT detector assembly 108.

In one exemplary embodiment, the display 232 allows the operator to operate the CT imaging system 200, select imaging protocols, review and revise imaging protocol parameters, start an acquisition scan, evaluate imaged data, view measured and/or estimated data and/or curves, trigger aspects of contrast scans, and the like. The display 232 may also allow the operator to select a region of interest (ROI) and/or request patient information, for example, via a graphical user interface (GUI) for a subsequent scan or processing.

Figure 3:
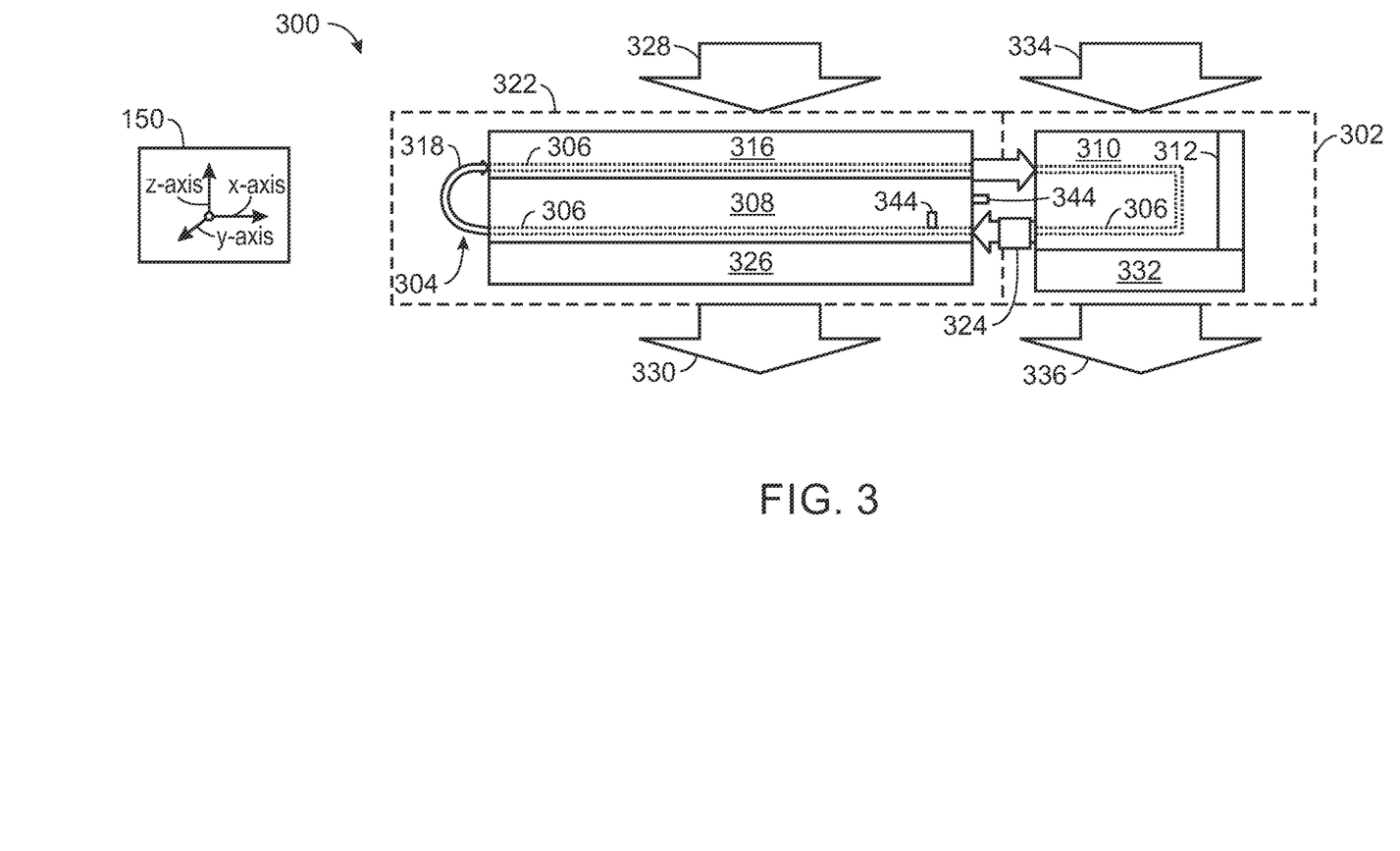
FIG. 3 is a schematic block diagram of an exemplary thermal management system for a CT imaging system.

FIG. 3 illustrates a schematic block diagram of an exemplary thermal management system 300 for use in a CT imaging system. The thermal management system 300 is an exemplary embodiment of the thermal management system 250, shown in FIG. 2. As such, the thermal management system described herein may share common structural and/or functional features. Furthermore, it will be understood that certain components (e.g., a liquid coolant pump 324, a first plurality of fans 332, a second plurality of fans 326) in the thermal management system 300 may be controlled via a suitable controller such as the thermal management system controller 213, shown in FIG. 2 or a liquid coolant temperature controller 312. The thermal management system controller 213 and the liquid coolant temperature controller 312 described herein may be the same system or two different systems that share common structural and/or functional features.

The thermal management system 300 includes a liquid cooling assembly 302 designed to liquid cool selected components in the CT imaging system such as a plurality of CT detector modules. The working fluid or liquid coolant of the liquid cooling assembly 302 may be water, in one exemplary embodiment. In another exemplary embodiment, the working fluid may be a heat transfer fluid such as a water glycol mixture, a dielectric fluid, a refrigerant or another known heat transfer fluid. The liquid cooling assembly 302 includes a coolant circuit 304 with coolant conduits 306 routing liquid coolant through the CT detector assembly 308. Various flow patterns used to route liquid coolant to the CT detector modules have been envisioned, such as series flow arrangements, parallel flow arrangements, serpentine flow arrangements, or combinations of series, parallel or serpentine flow arrangements, etc.

The liquid cooling assembly 302 further including a heat exchanger 310, a liquid coolant temperature controller 312, a liquid coolant pump 324, and a first plurality of fans 332 to provide temperature controlled liquid cooling for a plurality of CT detector modules. The liquid cooling assembly 302 is a closed loop liquid cooling system. Liquid coolant is cooled by the first plurality of fans 332 pulling or pushing air across the coolant conduits 306 in the liquid cooling assembly 302 and the liquid coolant is pumped through the CT detector assembly 308 to cool the plurality of CT detector modules.

The coolant circuit 304 including the coolant conduits 306 routes liquid coolant through the heat exchanger 310 and the CT detector assembly 308 in a closed loop liquid cooling system. The heat exchanger 310 transfers heat from the liquid coolant to the outside air, thereby cooling the liquid coolant, which in turn cools the CT detector assembly. The heat exchanger 310 may be a liquid to air heat exchanger and may include suitable components for achieving the heat transfer functionality such as heat fins, internal coolant conduits, a housing, etc. System efficiency as well as the different component cooling targets may be taken into account when selecting the specific design of the heat exchanger 310. The heat exchanger 310 may be coupled to or integrated within the liquid coolant temperature controller 312. The liquid coolant temperature controller 312 may be designed to trigger and adjust the flowrate and/or temperature of liquid coolant through the coolant circuit 304 by commanding different components such as the liquid coolant pump 324, the first plurality of fans 332, and/or one or more valves, etc., in the liquid cooling assembly 302. As such, the liquid coolant temperature controller 312 may include suitable hardware such as a processor, memory, etc., for triggering the flowrate and temperature adjustment.

The first plurality of fans 332 pulls or pushes air across the coolant conduits 306 and the heat exchanger 310. Inlet air indicated by arrow 334 enters the liquid cooling assembly 302 and is pulled or pushed across the coolant conduits 306 and the heat exchanger 310 by the first plurality of fans 332 and exhaust air indicated by arrow 336 exits the liquid cooling assembly 302. The plurality of fans or fan described herein may include components such as blades, motors generating rotational output, etc., to allow for airflow generation and adjustability.

As mentioned previously, a liquid coolant pump 324 may also be included in the liquid cooling assembly 302. The Liquid coolant pump 324 is designed to adjust the level of coolant flow through the coolant circuit 304. To accomplish the flow adjustment functionality the liquid coolant pump 324 may have conventional components such as pistons, pumping chambers, impellers, vanes, a housing, etc. The liquid coolant pump 324 is shown positioned in a conduit 306 between the CT detector assembly 308 and the heat exchanger 310. However, the liquid coolant pump 324 may be positioned in numerous suitable locations along the coolant circuit 304, such as for example, within or adjacent to the liquid coolant temperature controller 312. The liquid coolant temperature controller 312 may be designed to trigger adjustment of coolant flow through the coolant circuit 304 via adjustment of the pump 324, a valve, etc. In one exemplary embodiment, the liquid coolant temperature controller 312 may include a refrigeration assembly designed to remove additional heat from the liquid coolant. In this way, additional cooling can be leveraged by the thermal management system.

Liquid coolant in the coolant circuit 304 is routed from the heat exchanger 310 through the CT detector assembly 308, including the CT detector modules and readout electronics. It will be understood that one or more coolant conduits may be used to route liquid coolant from the heat exchanger 310 through the CT detector assembly 308.

The coolant circuit 304 also routes liquid coolant through the CT detector assembly 308 and through a rail radiator 316 (e.g., a heat exchanger), denoted by arrow 318. In other exemplary embodiments, the rail radiator 316 may be referred to as a heat exchanger. The rail radiator 316 is a liquid to air heat exchanger and may include suitable components for achieving the heat transfer functionality such as heat fins, internal coolant conduits, a housing, etc. However, it will be appreciated that the heat exchanger 310 may have a different configuration than the rail radiator 316. For instance, the sizing, profile, coolant conduit flow path, heat fin arrangement, etc., may vary between the heat exchangers to allow the heat exchangers to achieve different degrees of heat transfer. However, in other examples, the heat exchangers may be substantially equivalent in form, which may in some cases reduce manufacturing costs. It will also be appreciated that the rail radiator 316 may exhaust air to the detector hardware (e.g., readout electronics).

In other examples, liquid coolant may be routed through additional heat exchangers and/or other components before returning to the heat exchanger 310. Routing liquid coolant through multiple heat exchangers allows the liquid coolant to be cooled in multiple stages. Consequently, in certain exemplary embodiments, the heat exchangers may be downsized while achieving comparable cooling to a system deploying a single heat exchanger. In other exemplary embodiments, however, the heat exchangers may provide increased cooling of the components in the CT imaging system. Furthermore, an air cooling assembly 322, discussed in greater detail herein, may also take advantage of the staged cooling in the liquid cooling assembly 302 by synergistically using air directed across the rail radiator 316 to cool detector hardware (e.g., readout electronics).

The thermal management system 300 further includes an air cooling assembly 322 integrated within the CT detector assembly 308 and coupled to the liquid cooling assembly 302. The air cooling assembly 322 includes a second plurality fans 326 designed to pull or push air across a rail radiator 316, such as a heat exchanger coupled to the CT detector assembly 308, including the CT detector components, readout electronics or other detector hardware components.

The second plurality of fans 326 pull or push air across the rail radiator 316, the coolant conduits 306 and the CT detector assembly 308. Inlet air indicated by arrow 328 enters the air cooling assembly 322 and is pulled or pushed across the rail radiator 316, coolant conduits 306 and the CT detector assembly 308 by the second plurality of fans 326 and exhaust air indicated by arrow 330 exits the air cooling assembly 322. Each of the plurality of fans described herein may include components such as blades, motors generating rotational output, etc., to allow for airflow generation and adjustability.

In some examples, the air cooling assembly 322 may be integrated within an enclosure 340 of the CT detector assembly 308. In one example, air may be introduced into the enclosure at selected locations, denoted by inlet air arrow 328. Further, in another example, inlet air provided to the enclosure may be pre-conditioned. That is to say, that the inlet air may be cooled via a chiller prior to entering the enclosure.

In one example, exhaust air 336 from the first plurality of fans 332 of the liquid cooling assembly 302 may be routed to the inlet air 328 of the air cooling assembly 322. However, in other examples, the inlet air 328 and exhaust air 330 or the air cooling assembly 322 and the inlet air 334 and the exhaust air 336 of the liquid cooling assembly 302 may be fluidly decoupled.

Temperature sensors 344 may be coupled to certain components of the CT detector assembly 308 and the coolant conduits 306. However, additional or alternative temperature sensor locations may be possible.

In one exemplary embodiment, liquid coolant may be routed through a rail (e.g., a mounting structure) serving as a mounting structure for the plurality or array of CT detector modules of the CT detector assembly in the CT imaging system. However, liquid coolant may additionally or alternatively, be routed through conduits integrated within the CT detector assembly, in other embodiments.

In some instances, the liquid cooling system may be used to selectively cool components with higher cooling requirements, such as the CT detector modules, while the air cooling system may be used to cool components with lower cooling requirements, such as the readout electronics coupled to the CT detector modules. As a result, the CT detector assembly may be efficiently cooled while achieving the varied cooling requirements of the different components, thereby reducing the likelihood of component degradation caused by thermal overloading.

Figure 4:
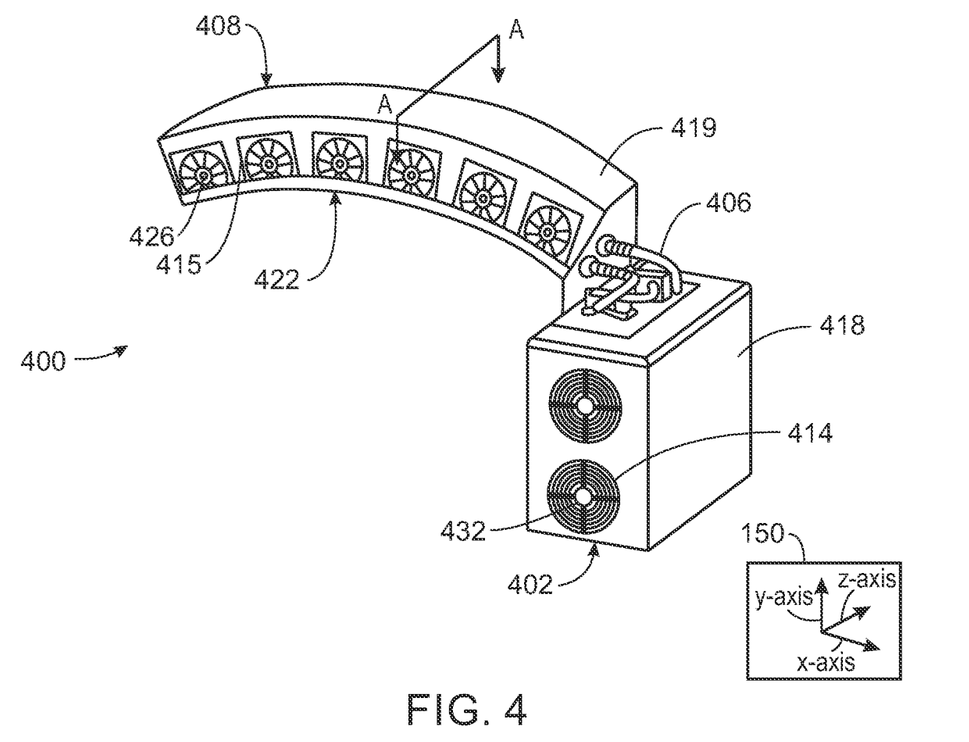
FIG. 4 is a perspective view of certain components of an exemplary thermal management system for a CT detector assembly of a CT imaging system.

FIG. 4 illustrates certain components of an exemplary thermal management system 400 for a CT detector assembly 408 of a CT imaging system. The CT imaging system includes a gantry that is designed to rotate around an object (e.g., a patient) being imaged during operation. Different gantry components have been removed from FIG. 4 to reveal underlying components of the thermal management system 400.

The thermal management system 400 is a hybrid cooling system for a CT detector assembly 408 that includes the combination of a liquid cooling assembly 402 and an air cooling assembly 422. These two different cooling assemblies 402, 422 may be coupled together to create a cooler temperature for the CT detector assembly 408. The liquid cooling assembly 402 is coupled to the air cooling assembly 422 with a plurality of liquid coolant conduits 406.

The thermal management system 400 includes a liquid cooling assembly 402 having a first plurality of fans 432 and an air cooling assembly 422 having a second plurality of fans 426.

Each fan in the first plurality of fans 432 is positioned in an opening 414 of an enclosure 418. The enclosure 418 may enclose a heat exchanger, a liquid coolant temperature controller, coolant conduits, a liquid coolant pump, temperature sensors, etc. Each fan in the second plurality of fans 426 is positioned in an opening 415 of an enclosure 419. The enclosure 419 may enclose a CT detector assembly (e.g., CT detector modules, which may include X-ray sensors, readout electronics, etc.), coolant conduits, temperature sensors, and other CT detector assembly components. The second plurality of fans 426 is spaced apart from the first plurality of fans 432.

Figure 5:
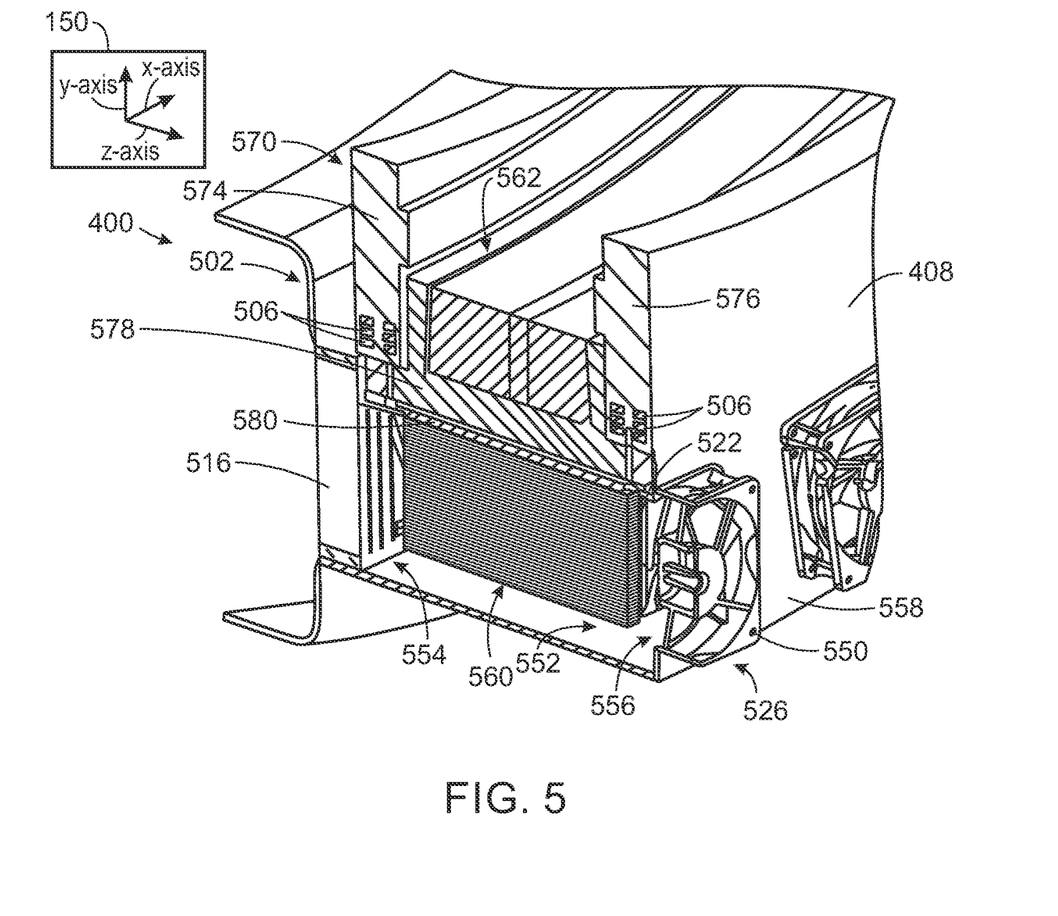
FIG. 5 is a cross-sectional perspective view of a portion of the exemplary CT detector assembly with the thermal management system for a CT imaging system cut along line A-A of FIG. 4.

FIG. 5 illustrates a cross-sectional perspective view of a portion of the exemplary CT detector assembly 408 illustrating an exemplary embodiment of a thermal management system 400 for a CT imaging system cut along line A-A of FIG. 4.

The thermal management system 400 includes an air cooling assembly 522 including a plurality of fans 526. At least one fan 550 in the plurality of fans 526 is positioned in a bottom portion 552 of the CT detector assembly 408 and attached to an output opening 556 in a first sidewall 558 of the CT detector assembly 408. The at least one fan 550 may be positioned in an input opening 554 or an output opening 556 of an airflow duct 560. The airflow duct 560 is shown extending from the input opening 554 to the output opening 556. It will be appreciated that the airflow duct 560 may also be contoured to form a common duct with the other fans in the plurality of fans, in some embodiments. However, in other examples, the airflow duct may have other suitable contours.

The plurality of fans 526 may be adjusted to alter the amount of air traveling through the airflow duct 560. The airflow duct 560 is positioned adjacent to a plurality of or array of CT detector modules 562. Specifically, in the illustrated embodiment, the airflow duct 560 is shown positioned radial outward from the CT detector modules 562. However, other relative positions between the CT detector modules and the airflow passage have been contemplated. Furthermore, the airflow duct 560 may traverse the CT imaging system in a direction parallel to a rotational axis of the gantry. However, other suitable airflow duct arrangements have been contemplated.

The thermal management system 400 includes a rail radiator 516 (e.g., heat exchanger) that is positioned in the input opening 554 of the airflow duct 560. The rail radiator 516, shown in FIG. 5 may be similar to the rail radiator 316, shown in FIG. 3. The rail radiator 516 allows greater amounts of thermal energy to be removed from the coolant circuit. As such, by including a rail radiator in the coolant circuit, the capability of the liquid cooling assembly can be extended, enabling the CT detector modules to be cooled by a greater amount, if desired. Furthermore, by deploying two heat exchangers in the coolant circuit, the liquid coolant temperature controller 312, shown in FIG. 3, may experience a smaller thermal load.

It will be understood that the rail radiator 516 is designed to allow air to flow therethrough and therefore may include coolant conduits, gaps or openings, etc. However, the rail radiator 516 may be positioned in an intermediary location in the airflow duct 560, in other embodiments.

Detector hardware components, such as readout electronics 522 may be positioned in the airflow duct 560. The detector hardware components 522 are electronically coupled to the CT detector modules 562. The rail radiator 516 may be positioned between the detector hardware components 522 and the CT detector modules 562 to reduce conductive heat transfer.

There is a thermal barrier 580 between the CT detector modules 562 and the detector hardware components 522, such as the readout electronics.

The thermal management system 400 further includes a liquid cooling assembly 502 including a rail 570 (e.g., a mounting structure) serving as a mounting structure for the plurality or array of CT detector modules 562. The rail 570 includes a plurality of coolant conduits 506 extending therethrough for liquid coolant to flow.

In one embodiment, the rail 570 may be constructed out of a metal (e.g., aluminum, steel, etc.) to increase conductive heat transfer between the CT detector modules 562 and the rail 570. However, the rail 570 may be constructed out of other suitable materials, such as polymeric materials, in other embodiments.

The rail 570 is designed to have CT detector modules 562 mounted thereto. Thus, the rail 570 serves as a mounting structure for the CT detector modules 562. The rail 570 is shown including a first radial section 574 and a second radial section 576 with the CT detector modules 562 positioned therebetween. Thus, the CT detector modules 562 may be positioned axially between the first and second radial sections 574, 576. Furthermore, the radial sections 574, 576 may be discretely arranged on opposing sides of the CT detector modules 562. However, in other examples, a base 578 may extend between the two radial sections 574, 576, thereby forming a continuous structure.

Directing coolant through the plurality of coolant conduits 506 extending through the two radial sections 574, 576 of the rail 570 and having the CT detector modules 562 coupled thereto, allows the CT detector modules 562 to be cooled by a greater amount when compared to air cooling the CT detector modules. Consequently, the CT detector modules may be operated within a targeted temperature range to reduce the likelihood of detector thermal degradation.

The coolant conduits 506 traverse both the first radial section 574 and the second radial section 576 of the rail 570. To elaborate, the coolant conduits in the first radial section 574 may have conduits exhibiting a counterflow arrangement. The coolant conduits in the second radial section 576 may exhibit a similar flow pattern. Consequently, the temperatures of the rail sections may be more balanced to reduce the chance of unequal thermal warping of the opposing rail sections.

Deploying a hybrid style thermal management system provides the CT imaging system with the ability to deploy granular and asymmetric cooling of selected components in the CT imaging system to allow the components to operate more effectively and efficiently. Thus, in one example, the CT detector modules, which may include X-ray sensors may be cooled to a greater degree than the readout electronics due to their disparate cooling targets.

Figure 6:
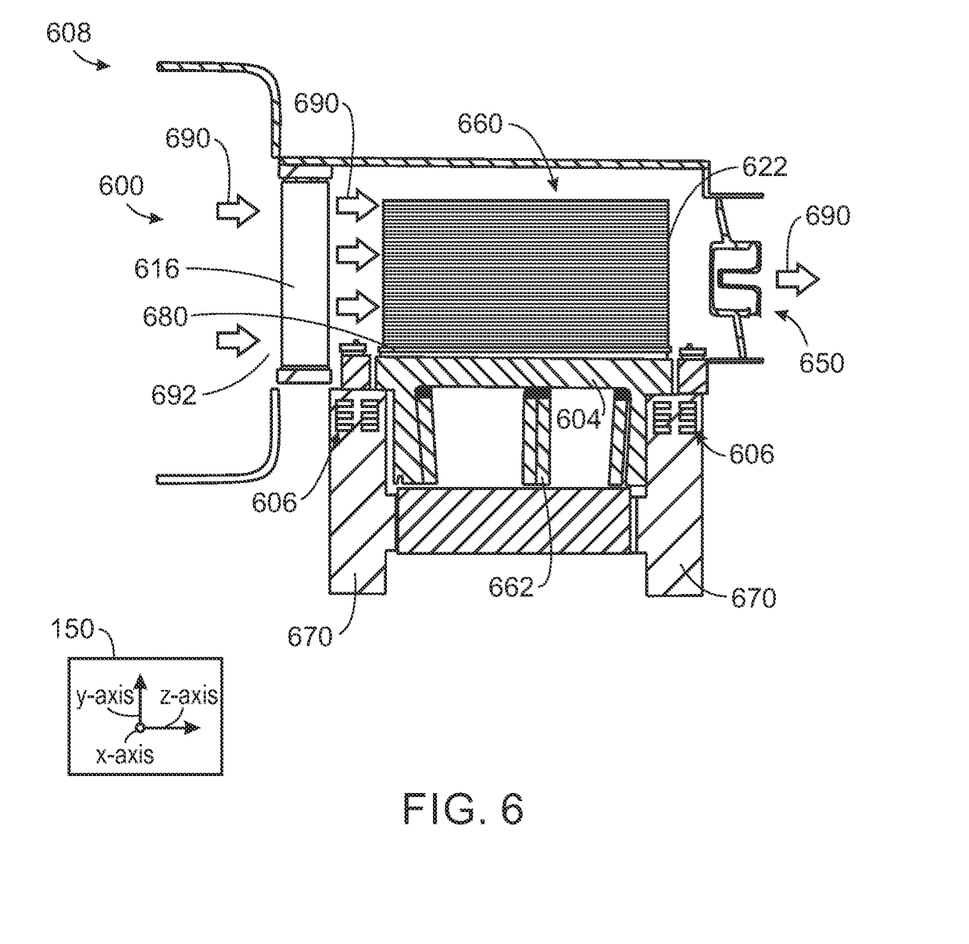
FIG. 6 is a cross-sectional side view of the exemplary CT detector assembly with the exemplary thermal management system, depicted in FIGS. 4 and 5.

FIG. 6 illustrates a cross-sectional side view of the exemplary CT detector assembly 608 with an exemplary thermal management system 600 similar to the thermal management system 500 illustrated in FIG. 5.

Arrows 690 indicate the general direction of airflow into the airflow duct 660, through the airflow duct 660, and out of the airflow duct 660 through the at least one fan 650. To elaborate, initially air is drawn into the airflow duct 660 at location 692. Drawing air from the location may allow cooler air to enter the airflow duct 660 when compared to other potential air reservoir locations. Air passes through the rail radiator 616 and then travels through/around detector hardware components 622, such as the readout electronics positioned in the airflow duct 660. Air then exits the airflow duct 660 through the at least one fan 650. Routing the outflow of the rail radiator 616 to the detector hardware components 622 enables additional heat to be drawn out of the coolant circuit. In this way, airflow generated by at least one fan can both cool readout electronics and the liquid coolant circuit, increasing CT imaging system operating and space efficiency, if desired. However, in other examples, the rail radiator 616 may be spaced away from the airflow duct 660.

The rail radiator 616 may be arranged between the CT detector modules 662 and the detector hardware components 622. Additionally or alternatively, a thermoelectric cooler may be positioned between the CT detector modules 662 and the detector hardware components 622. In this way, additional cooling of the CT detector modules 662 and/or corresponding hardware components 622 may be achieved. Additional or alternative thermoelectric coolers may be provided in the thermal management system 600 such as within the rail 670, the detector hardware components 622, digital tomography equipment in the CT imaging system, etc., to facilitate additional component cooling. In certain exemplary embodiments, heat sinks may be coupled to the rail 670 to direct even more heat away from the rail 670 and the CT detector modules and X-ray sensors. The rail 670 includes a plurality of coolant conduits 606 extending therethrough for liquid coolant to flow. In addition, there is a thermal barrier 680 between the CT detector modules 662 and the detector hardware components 622, such as the readout electronics.

The increase cooling provided by the thermal management system may allow X-ray sensors with larger cooling needs to be deployed in the CT imaging system, if desired. For instance, photon-counting X-ray sensors may be used in the CT imaging system to improve sensing capabilities. Additionally, in certain exemplary embodiments the CT detector modules may be duty cycled to reduce module power consumption. In such an embodiment, the increased cooling provided by the liquid coolant routed through the rail adjacent to the CT detectors enables possible thermal instability caused by the duty cycling to be diminished.

Different control strategies for the thermal management system have been envisioned such as feedback type control strategies, in certain exemplary embodiments, or open-loop control strategies, in other embodiments. Different control strategy variants are expanded upon herein with regard to FIGS. 7-9.

Figure 7:
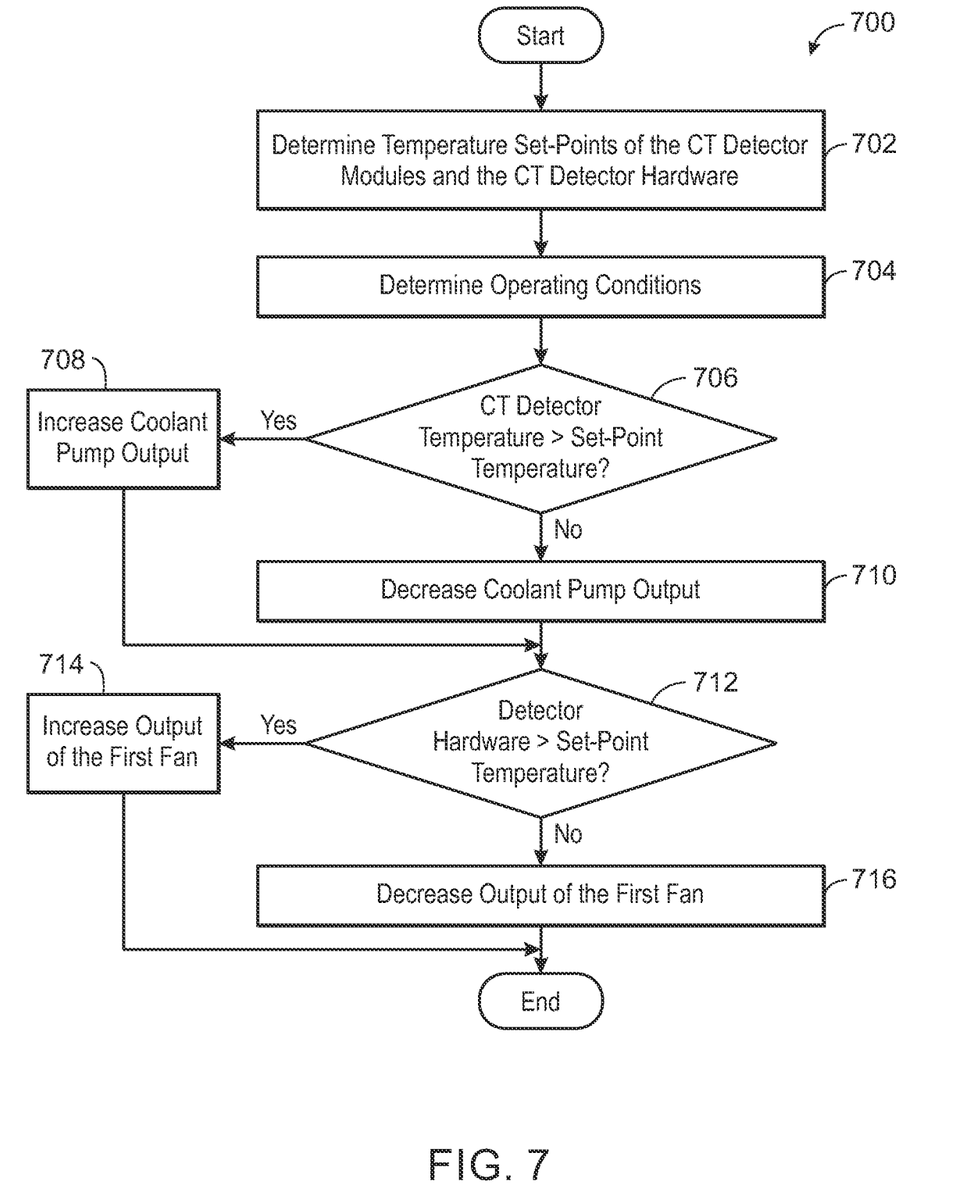
FIG. 7 is a flow diagram of an exemplary method for operation of a thermal management system for a CT imaging system.

FIG. 7 illustrates a flow diagram of an exemplary method 700 for operating a thermal management system for a CT imaging system. The method 700 as well as the other control strategies herein may be implemented by any of the systems, machines, components, devices, etc., described above with regard to FIGS. 1-6. However, in other examples, the method 700 may be carried out by other suitable systems, machines, components, devices, etc. Instructions for carrying out method 700 and/or the other methods described herein may be at least partially executed by a processor based on instructions stored in memory (e.g., non-transitory memory).

At step 702, the method may include determining temperature set-points of the CT detector modules and the CT detector hardware. In one example, the temperature set-points may be predetermined values stored in memory. In such an example, determining the set-points may involve retrieving the set-points from a data structure. However, dynamic generation of control set-points based on ambient conditions, CT imaging system operating conditions, etc., for instance, have been envisioned. The temperature set-points may be calculated based on the material construction of the components, circuit layout, component power consumption, expected temperature dependent operational efficiency, etc. It will be understood that the set-points may be non-zero value. Specifically, in one example, the temperature set-point of the detector hardware may be greater than the temperature set-point of the CT detector module. In one use-case example, the detector set-point may be between 45° C. and 55° C. and the hardware set-point may be between 65° C. and 75° C.

At step 704, the method includes determining CT imaging system operating conditions such as CT detector module temperature, coolant temperature, CT detector hardware temperature, ambient temperature, CT imaging system power consumption, etc.

At step 706, the method includes determining if the CT detector module temperature is above its corresponding temperature set-point or outside a predetermined temperature range. For example, signals may be gathered from X-ray sensors coupled or adjacent to the corresponding components. Additionally or alternatively, the temperatures of the different thermal management system components may be modeled.

If the CT detector module temperature is greater than the set-point (YES at step 706) the method proceeds to step 708 where the method may include increasing the coolant pump output. In some examples, the degree to which the coolant pump speed is increased may be selected based on the difference between the temperature set-point and the CT detector module temperature. However, in other instances, the coolant pump may be simply placed at or near its maximum output value.

Conversely, if it is ascertained that the CT detector module temperature is not above the set-point (NO at step 706) the method moves to step 710 where the method may include decreasing the coolant pump output. Again, the amount the coolant pump speed reduction may be dependent on the difference between the set-point and the CT detector temperature or the coolant pump may be turned off, in some instances. At step 712 the method may include determining if the CT detector hardware temperature is above its corresponding temperature set-point.

If the CT detector hardware is above the temperature set-point (YES at step 712) the method advances to step 714 where the method may include increasing output of the first plurality of fans or fan. In this way, airflow through the airflow duct containing the CT detector hardware and the rail radiator is increased to increase hardware cooling as well as increase the amount of heat removed from the coolant circuit. If the CT detector hardware is not above the temperature set-point (NO at step 712) the method moves to step 716. At step 716 the method may include decreasing the output of the first plurality of fans or fan. Again, the amount of fan speed increase/decrease may be selected based on the difference between the hardware temperature and the associated set-point.

The method 700 may comprise a high-level feedback control strategy. However, strategies that are more complex may be used for feedback control such as a proportional-integral-derivative (PID) control scheme where an error value representing the difference between a set-point and a process variable is calculated, for example.

Figure 8:
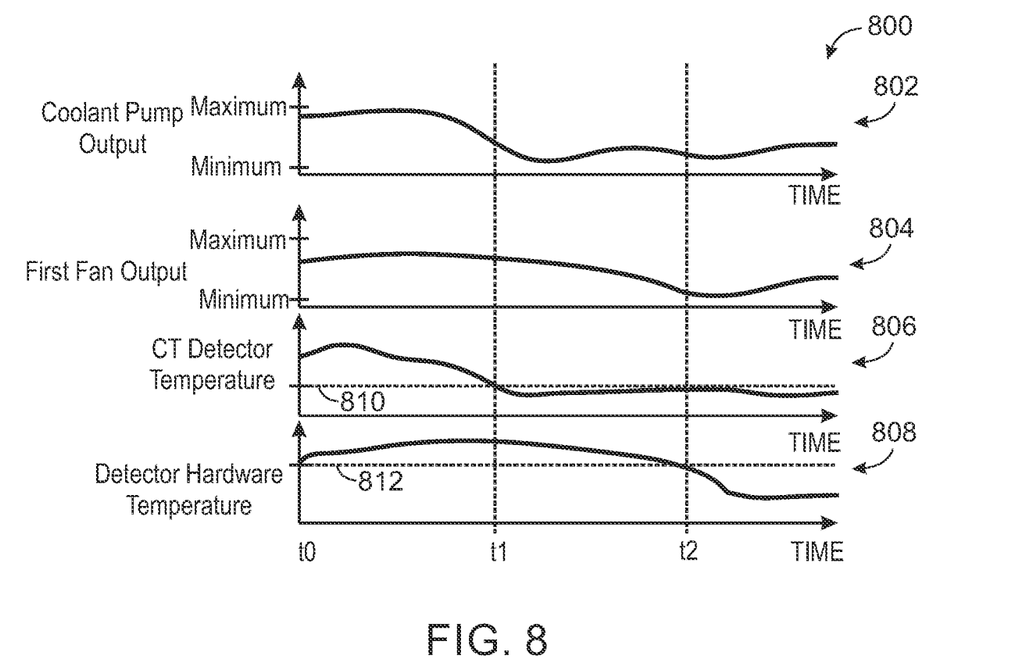
FIGS. 8 and 9 are graphical representations of different use-case control techniques for a thermal management system.
Figure 9:
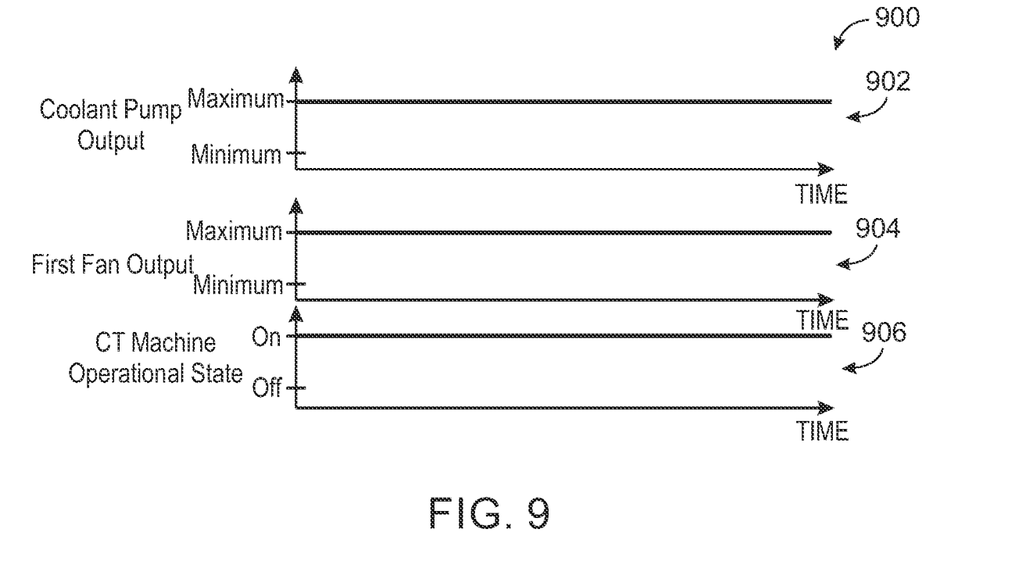

FIGS. 8 and 9 illustrate two different graphical representations 800, 900 of two different use-case control techniques for a thermal management system. In each graph, time is indicated on the horizontal axis. Although specific numerical time values are not indicated on the horizontal axis it will be understood that relative timing of different steps, events, etc., may be ascertained from the graphs. FIG. 8 illustrates a feedback control technique for the thermal management system, while FIG. 9 illustrates a less nuanced control technique where relatively high levels of component cooling is desired.

Referring specifically to FIG. 8, graph 802 indicates an output of the coolant pump, where coolant pump output values are indicated on the vertical axis. In particular, a "Maximum" and a "Minimum" coolant pump output values are indicated on the vertical axis. Additionally, graph 804 indicates an output of the first plurality of fans or fan, where the fan output values are indicated on the vertical axis. In particular, a "Maximum" and a "Minimum" fan output values are indicated on the vertical axis. The maximum coolant pump and/or fan output values may correspond to practical maximum outputs established in the thermal management system to avoid coolant pump/fan degradation, remain within desirable levels of power consumption, etc.

Graph 806 indicates CT detector temperature where CT detector temperature is indicated on the vertical axis and graph 808 indicates detector hardware temperature (e.g., readout electronic temperature) on the vertical axis. A set-point 810 of CT detector temperature and a set-point 812 of detector hardware temperature are also illustrated in FIG. 8. The CT detector set-point is larger than the hardware set-point, in the illustrated use-case example. For example, the detector set-point may be 70° C. while the hardware set-point may be 50° C. However, numerous suitable set-point values have been envisioned and may be dependent on the type of detector and hardware components used in the CT imaging system, the layout of the CT imaging system, ambient temperature, etc. Thus, the components have varied cooling needs. Fan and coolant pump control are adjusted to enable the thermal management system to achieve the asymmetric cooling needs of the detector and detector hardware. As illustrated, coolant pump speed is adjusted using a feedback control strategy where coolant pump speed is increased when detector temperature is above the set-point and when lower than the set-point coolant pump speed is decreased. The first plurality of fans or fan is adjusted in a similar fashion. The coolant pump and fan are operated in a continuous manner as illustrated in FIG. 8. However, discrete adjustment control techniques of the coolant pump and/or the fan have been envisioned. For example, the coolant pump or fan may be placed at or near maximum output when the associated component is above the set-point temperature and may be placed at a lower output level (e.g., baseline output) when the associated component is below the set-point temperature.

Referring specifically to FIG. 9, graph 902 indicates an output of the coolant pump, where coolant pump output values are indicated on the vertical axis. In particular, a "Maximum" and a "Minimum" pump output values are indicated on the vertical axis. Additionally, graph 904 indicates an output of the first plurality of fans or fan, where fan output values are indicated on the vertical axis. In particular, a "Maximum" and a "Minimum" fan output values are indicated on the vertical axis. The maximum pump and fan output values may correspond to practical maximum outputs established in the thermal management system to avoid coolant pump/fan degradation, remain within desirable levels of power consumption, etc. Graph 906 indicates CT imaging system operational state where operational values of "On" and "Off" are indicated on the vertical axis. As depicted in FIG. 9, the coolant pump and the fan are placed at their maximum output values during operation to achieve a relatively high level of detector and readout hardware cooling.

A technical effect of providing a thermal management system in a CT imaging system using air cooling to remove heat from CT hardware and coolant in a coolant circuit is increasing the system's operational efficiency and achieving asymmetric cooling of different components, if desired.

In another representation, a thermal management system for cooling a CT detector assembly of a CT imaging system. The thermal management system includes an air cooling sub-system designed to air cool the readout electronics of the CT detector assembly and a liquid cooling sub-system including a coolant loop circulating coolant through a CT detector assembly housing a plurality of CT detector modules including X-ray sensors of the CT detector assembly. The air and liquid cooling sub-systems may be coupled together in the thermal management system to cool the components of the CT detector assembly.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one exemplary embodiment" or "an exemplary embodiment" of the present disclosure are not intended to be interpreted as excluding the existence of additional embodiments that also incorporate the recited features. As described herein "approximately" and "substantially" refer to values of within plus or minus five percent, unless otherwise noted.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. A thermal management system for a computed tomography (CT) imaging system, the thermal management system comprising:
    a liquid cooling assembly including a liquid coolant pumped through a closed loop conduit from a heat exchanger and a liquid coolant temperature controller through a CT detector assembly and back to the heat exchanger and liquid coolant temperature controller, the liquid cooling assembly including a first plurality of fans configured to pull inlet air from outside to flow over the closed loop conduit with temperature control to cool the liquid coolant and exhaust air to outside of the thermal management system, wherein the liquid cooling assembly includes a liquid coolant circuit that traverses a first radial section and a second radial section of a rail, and wherein at least one CT detector module is positioned axially between the first radial section and the second radial section; and
    an air cooling assembly coupled to the liquid cooling assembly, the air cooling assembly including a second plurality of fans configured to pull inlet air from outside the thermal management system to flow over a rail radiator, the closed loop conduit, the CT detector assembly and exhaust air to outside of the thermal management system.

2. The thermal management system of claim 1, further comprising a pump coupled to the liquid coolant circuit to pump the liquid coolant through the closed loop conduit.

3. The thermal management system of claim 1, further comprising a thermal barrier positioned between the at least one CT detector module and a CT detector readout electronics.

4. The thermal management system of claim 1, wherein the liquid cooling assembly cools a plurality of CT detector modules.

5. The thermal management system of claim 4, wherein the liquid cooling assembly cools a plurality of X-ray sensors within the plurality of CT detector modules.

6. The thermal management system of claim 3, wherein the air cooling assembly cools the CT detector readout electronics.

7. The thermal management system of claim 1, wherein the liquid coolant is water.

8. The thermal management system of claim 1, wherein the liquid coolant is a refrigerant.

9. A thermal management system for a CT imaging system, the thermal management system comprising:
    a liquid cooling assembly including:
        a coolant conduit routing a liquid coolant from a heat exchanger to a rail and from the rail to a rail radiator and back to the heat exchanger; and
        a coolant pump coupled to the coolant conduit to pump the liquid coolant through the coolant conduit;
    a plurality of CT detector modules coupled to a first side of the rail;
    a plurality of detector hardware components coupled to a second side of the rail, positioned in an airflow duct, and in electronic communication with the plurality of CT detector modules; and
    an air cooling assembly including a plurality of fans positioned in a plurality of outlet openings in the airflow duct; and
    a rail radiator positioned in an inlet opening of the airflow duct.

* * * * *